United States Patent [19]

Rothaut et al.

[11] Patent Number: 4,576,790

[45] Date of Patent: Mar. 18, 1986

[54] LOW GOLD DENTAL ALLOYS

[75] Inventors: Josef Rothaut, Fort Lee, N.J.; Jürgen Hausselt, Langenselbold, Fed. Rep. of Germany; Rudi Steinke; Angela Klaus, both of Hanau, Fed. Rep. of Germany

[73] Assignee: Degussa Aktiengesellschaft, Frankfurt, Fed. Rep. of Germany

[21] Appl. No.: 695,814

[22] Filed: Jan. 28, 1985

[30] Foreign Application Priority Data

Feb. 24, 1984 [DE] Fed. Rep. of Germany ....... 3406711

[51] Int. Cl.$^4$ ............................................. C22C 5/04
[52] U.S. Cl. .................................. 420/464; 420/587; 420/589; 433/207
[58] Field of Search ............... 420/464, 580, 587, 589; 433/200, 207

[56] References Cited

U.S. PATENT DOCUMENTS

| | | | |
|---|---|---|---|
| 2,050,077 | 8/1936 | Wise | 420/587 |
| 3,667,936 | 6/1972 | Katz | 420/587 |
| 4,201,577 | 5/1980 | Ingersoll et al. | 420/587 |
| 4,387,072 | 6/1983 | Schaffer | 420/464 |
| 4,419,325 | 12/1983 | Prasad | 420/587 |
| 4,451,639 | 5/1984 | Prasad | 420/464 |

FOREIGN PATENT DOCUMENTS

| | | | |
|---|---|---|---|
| 2944755 | 5/1980 | Fed. Rep. of Germany . | |
| 0029424 | 3/1977 | Japan | 420/589 |
| 0099031 | 8/1978 | Japan | 420/589 |

*Primary Examiner*—L. Dewayne Rutledge
*Assistant Examiner*—Robert L. McDowell
*Attorney, Agent, or Firm*—Cushman, Darby & Cushman

[57] ABSTRACT

Low gold dental alloys, especially for firing on dental porcelains, should be easily worked, result in no discolorations and bubble formation in the firing, and have a physiologically replaceable hardness and a low melting interval. These properties are shown by alloys having 20 to 35 wt. % gold and 45 to 65 wt. % palladium if they also contain (a) 6 to 15 wt. % copper and 0 to 10 wt. % nickel,
(b) 0 to 12 wt. % indium, 0 to 12 wt. % tin, and 0 to 4 wt. % gallium, with the proviso that the sum of the content of indium and tin added to two and one-half times the gallium content must give a value between 5 and 15 wt. %,
(c) 0.1 to 1 wt. % iridium and/or rhenium and/or ruthenium, and
(d) optionally 0 to 1 wt. % aluminum, 0 to 1 wt. % tantalum, 0 to 1 wt. % titanium and/or 0 to 5 wt. % silver.

8 Claims, No Drawings

LOW GOLD DENTAL ALLOYS

BACKGROUND OF THE INVENTION

The invention is directed to low gold dental alloys, especially for firing on dental porcelains, the alloys containing 20 to 35 wt.% gold and 45 to 65 wt.% palladium.

For a long time there have been used in denistry crowns and bridges which have a metallic core and which are coated with a tooth colored ceramic. Such a combination compared to pure metallic crowns and bridges has advantages, both esthetically and physically, which result from the low heat conductivity of the ceramic. There have proven good for this purpose alloys having a high gold content which contain about 60 to 90 wt.% gold, about 1 to 15 wt% platinum, about 1 to 15 wt.% palladium, as well as silver, tin, indium, gallium, iron, and fine grain forming elements such as ruthenium, iridium, or rhenium. Because of the drastically increasing noble metal prices in the past years, these high gold content alloys have become extraordinarily expensive. For this reason and because of a general necessary reduction in cost in methods of health, therefore, there have been developed in recent times an entire series of low cost noble metal alloys which are suited for facing a dental ceramic. These include both alloys of reduced gold content based on gold-palladium or gold-palladium-silver with about 45 to 55 wt.% gold and also alloys based on palladium and palladium-silver which contain either no gold or only a few wt.% of gold.

Alloys for firing on dental porcelains must satisfy a number of requirements, such as, e.g., good castability, sufficient strength and ductility, compatibility of the elasticity and thermal coefficient of expansion of the alloys with the commercial dental ceramic compositions, as well as a sufficient, but not too high, hardness. Furthermore, these types of alloys must possess a sufficient strength at the firing temperatures of the ceramic. Besides, there must not occur undesired reactions between ceramic and the oxide layer of the alloy, especially discolorations and the formation of bubbles.

While high gold content alloys for the most part satisfy these requirements, practically all known reduced gold and gold free noble metal firing alloys have a more or less severe defect. Thus, the commercial alloys on the basis gold-palladium with a gold content between 45 and 55 wt.% almost without exception have a very high melting interval which in part exceeds the capacity of commercial casting apparatuses. A further weaknes endangering the success of a dental ceramic operation with this type of alloy is its very low thermal coefficient of expansion of, in part, less than $14.0 \times 10^{-6} K^{-1}$ which in unfavorable molding of the restoration or in subequent solder operations in faced metal ceramic parts can lead to cracks in the ceramic and also to spallings. The most severe disadvantage of these alloys, however, is in the inclination to form bubbles in the boundary surface between metal and ceramic after melting in the graphite crucible. The chief cause for this bubble formation is that the carbon taken up by the melt from the graphite crucible in the firing of the ceramic with oxides of the alloy or the ceramic burns to form carbon monoxide which remains behind as gas bubbles in the boundary surface (e.g., F. Sperner, dental-labor, Vol. XXX issue 12/1982, page 1733).

Alloys based on palladium are likewise associated with a large number of defects. For example, with these alloys the addition of alloying elements, which reduce the melting interval to the needed values lead to an unacceptable increase in hardness. With alloys based on palladium additionally because of their high palladium content and the susceptibility to carbon absorption associated therewith in no case can they be melted in a graphite crucible. The absorption of carbon would drastically increase the brittleness otherwise occurring with these alloys and besides make impossible a bubble free facing with dental ceramics.

In German OS No. 2944755 there are described numerous fired on alloys having about 32 to 63% gold and 29 to 58% palladium, which also contain indium and to which there can be added up to several percent of gallium, tin, copper, aluminum, titanium, and silver. The copper content in these alloys must be over 5%. However, it has been shown that even those alloys if they contain less than about 40% gold display very high liquidus temperatures (in part over 1400° C.). A reduction of the liquidus temperature through variation of the remaining additives leads to impermissible hardness valves.

Therefore, it was the problem of the present invention to provide low gold dental alloys, especially for firing on dental porcelains from 20 to 35 wt.% gold and 45 to 65 wt.% palladium, whose gold content should be clearly below the customary gold-palladium economical fired alloys which can be easily worked, correspond to the known dental porcelains in their thermal coefficient of expansion, in which there do not occur discoloration of the porcelain or bubble formation after melting in graphite crucibles and which compared to the known economical gold alloys above all should display a reduced hardness and a decreased melting interval.

SUMMARY OF THE INVENTION

This problem was solved according to the invention by additionally including in these alloys:
 (a) 6 to 15 wt.% copper and 0 to 10 wt.% nickel,
 (b) 0 to 12 wt.% indium, 0 to 12 wt.% tin, and 0 to 4 wt.% gallium, with the proviso that the sum of the content of indium and tin added to two and one-half times the gallium content must give a value between 5 and 15 wt.%,
 (c) 0.1 to 1 wt.% iridium and/or rhenium and/or ruthenium, and
 (d) optionally 0 to 1 wt.% aluminum, 0 to 1 wt.% tantalum, 0 to 1 wt.% titanium and/or 0 to 5 wt.% silver.

Surprisingly, it has been found that the use of 6 to 15 wt.% of copper and in a given case up to 10% nickel brings about the necessary reduction of the melting interval and likewise raises the thermal coefficient of expansion of the alloy, however, without causing a drastic increase in hardness customarily occurring even with small concentrations of this type of additive. Likewise, it is surprising that the black oxide color expected with such high copper containing alloys and which has been found to be disturbing for facing with ceramics does not occur with the alloys of the invention. Rather, there is observed a gray and firmly adhering oxide which at the same time causes an unusually good adhesion between the metal and the fired on dental ceramic. The total addition of copper and nickel should not exceed 16 wt.%.

It has been observed as a further surprising effect with copper containing alloys having more than 6 wt.% copper that by alloying with tin there can be reduced the carbon absorption of the melt from the graphite crucible. This positive influence of tin can be clearly strengthened by the addition of up to 1 wt.% of aluminum and/or titanium. Concentrations of aluminum and titanium over 1 wt.% lead to indefensible increases in hardness of the alloy. This relationship makes it possible to be able to face these alloys with dental ceramics without problem despite their high palladium content, even after melting in a graphite crucible, without bubbles caused by carbon occurring in the boundary area between metal and ceramic. This possibility to drastically reduce the absorption of carbon by the melt from the graphite crucible by an industrial alloying procedure is noteworthy insofar as previously known investigations have established an increasing tendency of the alloy with increasing palladium content when the alloy is in liquid form to absorb carbon. This relationship with the known gold reducing alloys frequently leads to bubbles in the ceramic, although these alloys containing 30 to 40 wt.% Pd are substantially lower in Pd.

With alloys that must not be melted in a graphite crucible, it is also possible to entirely or partially replace the alloying component tin by indium and/or gallium. All of the alloys can be worked without problems and an extraordinarily good flow and mold filling capability.

It has been surprisingly established that with the alloys of the invention, despite their high proportion of base metal components, there is shown an extraordinarily good corrosion behavior which is completely comparable with the high gold content alloys.

It is known that the addition of silver improves the workability of noble metal-dental alloys, especially improving their castability and solderability. Therefore, the alloys of the invention can also contain 0 to 5 wt.% silver. There is not observed a discoloration of the ceramic with these concentrations. Alloys have been proven especially advantageous, especially in regard to their hardness, coefficient of expansion and melting interval, in which the sum of the weight percents of the elements nickel, copper, indium, tin, gallium, and gold has a value between 23 and 28, whereby the gallium content is multiplied by a factor 2.5 and the gold content by a factor of 0.3. Thereby, nickel free alloys having 7 to 12 wt.% copper have proven to be especially good.

Unless otherwise indicated, all parts and percentages are by weight.

The alloys can consist of or consist essentially of the stated materials.

DETAILED DESCRIPTION

In the following table there are given the properties of several alloys according to the invention. The hardness thereby was measured after a calcining for 15 minutes at 700° C.

TABLE

| | Composition (wt. %) | | | | | | | | | | | Melting Interval | | Hardness/HV5 | |
|---|---|---|---|---|---|---|---|---|---|---|---|---|---|---|---|
| Nr | Au | Pd | Cu | Ni | In | Sn | Ga | Ti | Al | Ag | Ru | $T_L$ [°C.] | $T_S$ | Cast | Hard |
| 1 | 25 | 56.8 | 15 | — | — | — | 3 | — | — | — | 0.2 | 1242 | 1172 | 200 | 216 |
| 2 | 25 | 60.8 | 10 | — | — | 2 | 2 | — | — | — | 0.2 | 1318 | 1244 | 178 | 180 |
| 3 | 25 | 59.6 | 10 | — | 2 | — | 3 | — | — | — | 0.4 | 1298 | 1214 | 236 | 240 |
| 4 | 30.5 | 51.7 | 6.3 | — | 10.7 | 0.4 | — | — | — | — | 0.4 | 1313 | 1244 | 216 | 220 |
| 5 | 30 | 49.6 | 8.2 | — | — | 7.8 | — | — | — | 4 | 0.4 | 1266 | 1172 | 184 | 190 |
| 6 | 30 | 54.6 | 6.3 | — | 1.9 | 6.8 | — | — | — | — | 0.4 | 1298 | 1201 | 266 | 300 |
| 7 | 25 | 54 | 6 | 4 | — | 10.2 | — | 0.4 | — | — | 0.4 | 1218 | 1205 | 250 | 305 |
| 8 | 35 | 47.4 | 8.5 | — | — | 8.5 | — | — | 0.2 | — | 0.4 | 1236 | 1197 | 278 | 309 |

What is claimed is:

1. A low gold dental alloy, especially suitable for firing on dental porcelain consisting of 20 to 35 wt.% gold, 45 to 65 wt.% palladium and
   (a) 6 to 15 wt.% copper and 0 to 10 wt.% nickel,
   (b) 0 to 12 wt.% indium, 0 to 12 wt.% tin, and 0 to 4 wt.% gallium, with the proviso that the sum of the content of indium and tin added to two and one-half times the gallium content has a value between 5 and 15 wt.%,
   (c) 0.1 to 1 wt.% of at least one of iridium, rhenium, and ruthenium, and
   (d) 0 to 1 wt.% aluminum, 0 to 1 wt.% tantalum, 0 to 1 wt.% titanium, and 0 to 5 wt.% silver.

2. An alloy according to claim 1 wherein the sum of the weight percent of the elements nickel, copper, indium, tin, gallium, and gold is between 23 and 28, whereby the gallium content is multiplied by a factor of 2.5 and the gold content is multiplied by a factor of 0.3.

3. A dental alloy according to claim 2 containing 7 to 12 wt.% copper and free from nickel.

4. A dental alloy according to claim 1 containing 7 to 12 wt.% copper and free from nickel.

5. An alloy according to claim 1 which includes tin in an amount not greater than 12 wt.%.

6. An alloy according to claim 5 containing 0.4 to 12% tin.

7. An alloy according to claim 6 containing at least one of aluminum and titanium in an amount of 0.2 to 1%.

8. An alloy according to claim 5 including at least one of aluminum and titanium in an amount not greater than 1 wt.%.

* * * * *